United States Patent [19]
Ribier et al.

[11] Patent Number: 5,679,691
[45] Date of Patent: Oct. 21, 1997

[54] USE OF A SPIN TRAP IN A COSMETIC OR DERMATOLOGICAL COMPOSITION

[75] Inventors: Alain Ribier, Paris; Quang Lan Nguyen, Antony; Jean-Thierry Simonnet; Boudiaf Boussouira, both of Paris, all of France

[73] Assignee: L'Oreal, Paris, France

[21] Appl. No.: 597,101

[22] Filed: Feb. 6, 1996

Related U.S. Application Data

[62] Division of Ser. No. 366,748, Dec. 30, 1994, Pat. No. 5,569,663.

[30] Foreign Application Priority Data

Dec. 30, 1993 [FR] France .................... 93 15869

[51] Int. Cl.$^6$ .................... A61K 31/445; A61K 7/40; A61K 7/42
[52] U.S. Cl. .................... 514/315; 424/59; 424/60; 546/184
[58] Field of Search .................... 514/315; 424/59, 424/60; 546/184

[56] References Cited

U.S. PATENT DOCUMENTS

| | | | |
|---|---|---|---|
| 5,334,756 | 8/1994 | Likibi et al. | 562/565 |
| 5,352,442 | 10/1994 | Proctor | 424/70.1 |
| 5,569,663 | 10/1996 | Ribier et al. | 514/315 |

*Primary Examiner*—Shelley A. Dodson
*Attorney, Agent, or Firm*—Oblon, Spivak, McClelland, Maier & Neustadt, P.C.

[57] ABSTRACT

The invention relates to the use of a spin trap employed as an electron paramagnetic resonance measurement probe, in a cosmetic or dermatological composition for the light-protective, anti-ageing and/or anti-acne treatment of the skin. In particular, this spin trap is encapsulated in lipid vesicles which are capable of diffusing into the deep layers of the skin.

18 Claims, 1 Drawing Sheet

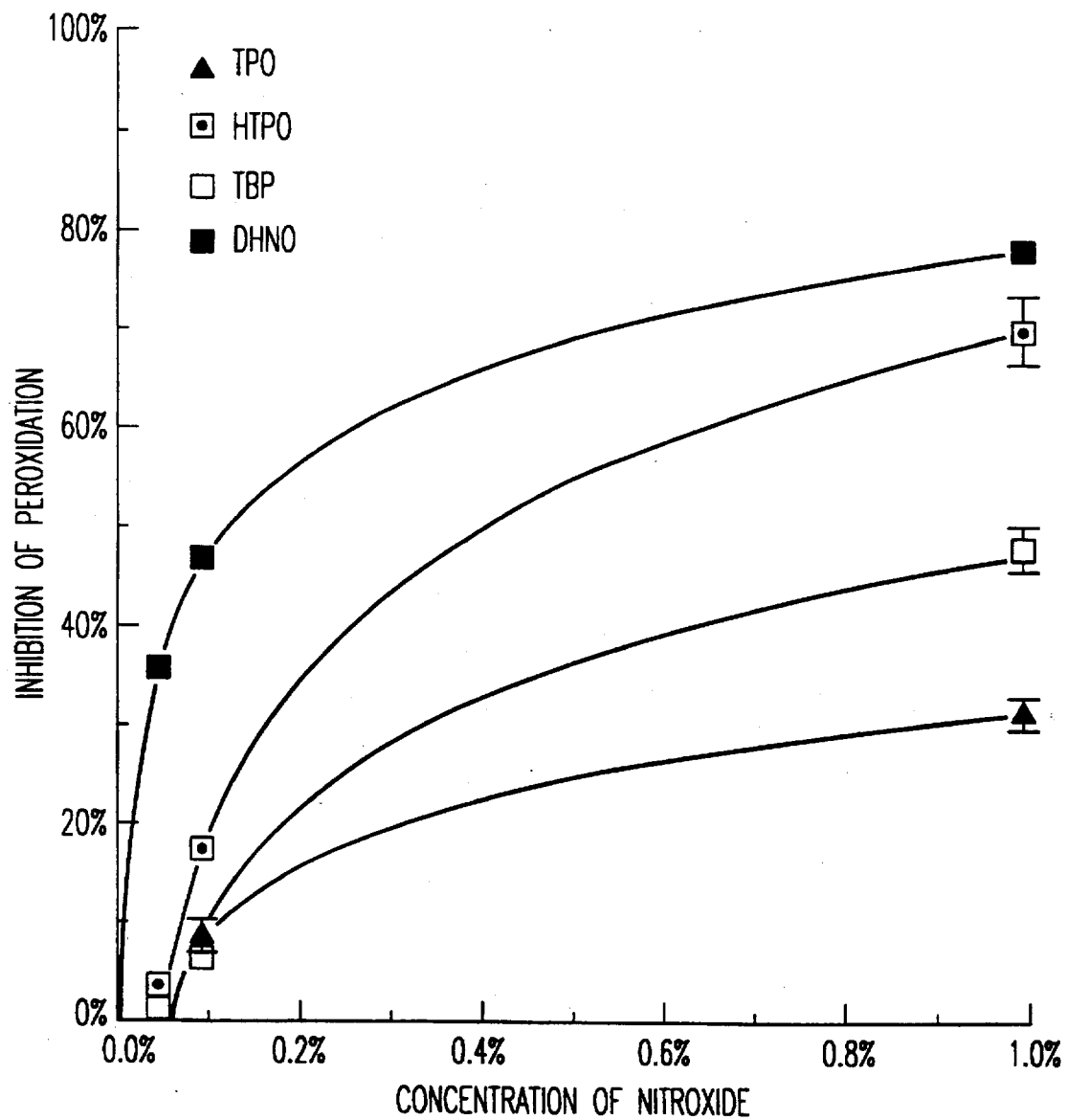

USE OF A SPIN TRAP IN A COSMETIC OR DERMATOLOGICAL COMPOSITION

This is a Division of application Ser. No. 08/366,748 filed on Dec. 30, 1994, now U.S. Pat. No. 5,569,663.

BACKGROUND OF THE INVENTION

1. Field of the Invention

The present invention relates to the use of a spin trap in a cosmetic and/or dermatological composition, for the light-protective, anti-ageing and/or anti-acne treatment of the skin, including the scalp. The invention also relates to a process for the topical cosmetic treatment of the skin and to a cosmetic and/or dermatological composition containing this spin trap.

2. Discussion of the Background

In order to provide an effective protection for the skin against sunlight, to reduce the effects of age and to eliminate the imperfections of the skin caused by ache, it is currently necessary to use several antioxidant active agents; at present, effective care of the skin against these effects and imperfections is obtained by incorporating 4 to 8 antioxidant active agents. However, the introduction of a large number of active agents into a cosmetic and/or dermatological composition complicates its manufacture, resulting particularly in an increase in the cost price thereof.

Consequently, the subject of the invention is a cosmetic and/or dermatological composition and the use thereof for the light-protective, anti-ageing and/or anti-ache treatment of the skin which enables these drawbacks to be overcome.

Spin traps and more especially nitroxide free radicals are generally used in spectroscopy as a probe for electron paramagnetic resonance (EPR), as described in the document "Electron paramagnetic resonance (EPR) imaging in skin: Biophysical and biochemical microscopy" by J. Fuchs et al., vol. 98, No. 5, 1992 p. 713 to 719 or U.S. Pat. No. 4,849,346. The measuring is based on the reduction of the spin traps.

Nitroxide free radicals are also used for displaying human organs by magnetic resonance study. More precisely, the subject of the invention is a use for the light-protective, anti-ageing and/or anti-acne treatment of the skin, of a spin trap employed as an electron paramagnetic resonance measurement probe, in a cosmetic or dermatological composition.

It has already been envisaged to inject a solution of N-tert-butyl-α-phenylnitrone into rodents for the purpose of lowering the level of oxidized proteins and of increasing the activity of glutamine synthetase and of neutral protease in their brains: see in this respect the document "Reversal of age-related increase in enzyme activity, and loss in temporal and spatial memory by chronic administration of the spin-trapping compound N-tert-butyl-α-phenylnitrone" by J. M. Carney et al., Proc. Natl. Acad. Sci. vol. 88, pp. 3633–3636, May 1991; however, this document does not in any way contemplate the use of this nitrone in a cosmetic and/or dermatological composition for an anti-ageing, anti-acne and/or light-protective treatment of the skin.

Moreover, it is known from document EP-A-0,327,263 to apply a composition containing a free-radical precursor and an adjuvant such as a reducing agent, an antioxidant or a hydroxyl-radical-sequestering agent to the scalp in order to stimulate hair growth. However, this document does not in any way teach the use of this free-radical precursor for the light-protective, anti-ageing and/or anti-ache treatment of the skin.

SUMMARY OF THE INVENTION

The Applicant has found, surprisingly, that it is possible to incorporate into cosmetic and/or dermatological skin treatment compositions spin traps having light-protective, anti-ageing and/or anti-acne properties.

Another subject of the invention is a cosmetic or dermatological composition for topical treatment, characterized in that it comprises a first dispersion of spherules which contain a spin trap used as an electron paramagnetic resonance measurement probe, and a cosmetically or dermatologically acceptable medium. This composition may be applied equally well to the human face and/or to the human body.

The composition of the invention advantageously contains a single spin trap, which facilitates its manufacture and lowers the manufacturing cost thereof compared with the compositions currently known for the light-protective, anti-ageing and/or anti-acne treatment of the skin. This is possible because the spin traps used in the invention have the advantage of being able to react with all the hydrophilic chemical radical species of oxygen, such as $O_2 \bullet^-$ and $OH \bullet$ and lipophilic radical species as $C_3 \bullet$, which are liable to form in the skin, whereas the active agents conventionally used in the cosmetic field, such as anti-oxygen-free-radical agents (vitamin E and BHT—tert-butylhydroxytoleune—for example) are specific for the $ROO \bullet$ type of radical, which is formed subsequent to initiation of the damage caused by the hydrophilic radical forms to the lipids of cutaneous cell membranes. However, the species $OH \bullet$ is the species most reactive towards biomolecules.

Hitherto, no one had made the connection between spin-trapping and light-protection, the combating of ageing and/or acne.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein: the single FIGURE attached represents curves showing the inhibition of the peroxidation of sebum (a lipidic liquid produced at the skin surface) by nitroxide radicals.

DETAILED DESCRIPTION OF THE PREFERRED EMBODIMENTS

Spin traps which may be used in the invention are especially nitroxide and nitrone radicals. In particular, these spin traps comprise one or more rings, at least one of which contains a nitrogen atom bonded to the oxygen atom..

The spin traps of the composition of the invention are, for example, those cited in the document by L. B. Volodarsky "Advances in the chemistry of stable nitroxides", Janssen Chimica Acta, vol. 8,, No 3f p. 12–19 (1990).

In particular, the spin trap of the invention as is chosen from the 2,2,6,6-tetramethylpiperidine 1-oxide, 4-hydroxytetramethylpiperidine 1-oxide, N-tert-butyl-alpha-phenylnitrone and doxylcyclohexane radicals, the salts of N-(1-oxyl-2,2,6,6-tetramethyl-4-piperidyl)-N,N-dimethyl-N-hydroxyethylammonium, such as ASL (N-(1-oxyl-2,2,6,6-tetramethyl-4-piperidyl)- N,N-dimethyl-N-hydroxyethylammonium iodide], and mixtures thereof.

The spin traps of the invention can be prepared by conventional methods known to those of ordinary skill in the art.

The spin trap is advantageously present in an amount of from 0.001% to 5% by weight relative to the total weight of the composition, better still in an amount of from 0.1% to 2% by weight.

According to the invention, the composition may be provided in the form of a gel, an emulsion, a serum or a lotion advantageously containing spherules which are preferably lipidic, or in the form of oil droplets dispersed by lipid vesicles. The use of non-lipid spherules is, however, possible; in this case, polymeric nanoparticles such as nanospheres and nanocapsules may be used.

The terms "lipid spherules or vesicles" are intended to refer to particles formed of a membrane consisting of one or more concentric lamellae, these lamellae containing one or more bimolecular layers of amphiphilic lipids encapsulating an aqueous phase. The aqueous phase may contain water-soluble active substances and the bimolecular layers of amphiphilic lipids may contain lipophilic active substances. These spherules generally have a mean diameter of between 10 nm and 5,000 nm.

The lipid spherules used in the invention are, in particular, spherules capable of releasing the spin trap into the deep layers of the skin, that is to say into the epidermis and the dermis. The reason for this is that the sites in the skin which are the most sensitive to radical species of oxygen are located in the epidermis and in the dermis. In particular, the radical species of oxygen cause considerable damage especially in cell membranes (membrane permeability), cell nuclei (mutation by the action on RNA or DNA) and in tissues (necroses, degeneration) resulting in cutaneous ageing; these species react with the various constituents of the skin.

Spherules capable of diffusing into the deep layers of the skin, also known as spherules with deep-down action, are found in particular in the gelled state at room temperature (20° C.). In addition, these spherules have a diffusion constant for encapsulated ASL in the *stratum corneum*, which constitutes the surface layers of the skin, of $>1\times10^{-7}$ $cm^2 s^{-1}$.

Measurement of the diffusion constant D is carried out by combining two methods using a paramagnetic probe, ASL: one-dimensional and periodic electron paramagnetic resonance (EPR), on the one hand, and EPR kinetic imaging, on the other hand. These two methods are respectively described in the articles "Evaluation of liposomes as drug carriers into the skin by one-dimensional EPR imaging" by V. Gabrijelcic et al., International Journal of Pharmaceutics, 62 (1990) p. 75–79, Elsevier, and "Liposome entrapped molecules penetration into the skin measured by nitroxide reduction kinetic imaging" by V. Gabrijelcic et al., Periodicum Biologorum vol. 93, No. 2, p. 245–246, (1991).

Moreover, these spherules with deep-down action have a strong encapsulating power.

Glucose is a labelling agent conventionally used for this type of determination (cf. in particular *Liposomes a practical approach* by R. R. C. New, IRL Press (1990), p. 125–136). The degree of encapsulation is expressed as the volume of glucose solution encapsulated in the spherules, measured in μl relative to the unit weight (mg) of the lipids constituting the membrane. This degree of encapsulation is determined immediately after the step of separation of the free glucose and of the encapsulated glucose ($T_0$), as well as twenty-four hours after this separation ($T_{24\ hours}$).

The difference between these 2 successive determinations illustrates the permeability of the spherules with respect to the encapsulated glucose.

The spherules (delivering the spin acceptor into the deep layers of the skin) have a high encapsulating power for the small water-soluble molecules which are conventionally modelled by glucose, this encapsulating power being maintained for at least 24 hours.

The spherules with deep-down action may be formed of lipids comprising at least one linear and saturated fatty chain having from 16 to 30 carbon atoms, such as hydrogenated phospholipids (from plants or from egg), saturated synthetic phospholipids such as dipalmitoylphosphatidylcholine, and polyol alkyl ethers or polyol alkyl esters containing one, two or three fatty chains per molecule. These lipids are used alone or as a mixture.

Another subject of the invention is a process for the topical application of the composition defined above for the anti-ageing, anti-acne and/or light-protective treatment of the skin.

According to the invention, the spin traps have the characteristic feature of reacting with chemical species of oxygen which have a very short lifetime and are thus highly reactive, that is to say with hydrophilic species of oxygen, which prevents, inter alia, the formation of ROO• radicals. They thus make it possible effectively to protect especially the lipids, proteins and nucleic acids (RNA and DNA) of the skin.

It is advantageously possible to combine a sunscreen agent with the spin trap in order to prevent the formation of singlet oxygen in the skin, during the action of sunlight on the skin, and thus to enhance the effectiveness of the composition of the invention in an anti-ageing, anti-acne and/or light-protective treatment of the skin. This screening agent may consist in particular of an anti-UVA-radiation and/or anti-UVB-radiation screening agent of hydrophilic or lipophilic organic nature, such as benzene-1,4-di(3-methylidene-10-camphorsulphonic) acid, or of inorganic nature, such as nanopigments ($TiO_2$); it especially provides protection for the surface of the skin, which is complementary to the deep-down protection.

To do this, the screening agent is preferably encapsulated in spherules, especially lipid spherules, which are capable of diffusing into the surface layers of the skin. These spherules, known as spherules acting at the surface, are in particular in the fluid state at room temperature (20° C.). Moreover, they provide a diffusion of ASL in the *stratum corneum* with a diffusion coefficient D of $<1\times10^{-7}$ $cm^{-2}s^{-1}$. In addition, they have a low encapsulating power. In other words, these spherules retain the encapsulated glucose for less than 24 hours.

Moreover, the two types of spherules may contain other types of cosmetic active agents, such as moisturizing agents (polyols and more particularly glycerine), keratolytic agents (5-n-octanoylsalicylic acid), anti-inflammatory agents, anti-microbial agents (triclosan), vitamins (A, C and F), proteins (amino acids, peptides and proteins), sugars (fructose), trace elements (Fe, Mg and Se), enzymes (lipases, proteases and DNA-repair enzymes), essential oils, etc.

The main lipids constituting the spherules which are active at the surface are chosen in particular from the group comprising ionic lipids, especially such as natural plant- or egg-based phospholipids containing unsaturated fatty chains having from 16 to 30 carbon atoms; nonionic lipids such as polyol alkyl ethers or polyol alkyl esters comprising one or more fatty chains per molecule, including at least one fatty chain with a length of less than 16 carbon atoms, such as lauryl polyglycery-6-cetearyl glycol ether and mixtures thereof. The latter ether is described in detail in Patent Application FR 92-09603 filed by L'Oréal.

It is possible, in a known manner, to incorporate into the lipid phase constituting the lipid membrane of the spherules, at least one additive chosen from the group formed of sterols (phytosterols, cholesterol or polyoxyethylenated phytosterols), long-chain alcohols, diols and triols (phytanetriol), long-chain amines and the quaternary ammonium derivatives thereof and/or an ionic additive chosen from the group formed of phosphoric esters of fatty alcohols and the alkali metal (Na or K) salts thereof, such as dicetyl phosphate, sodium dicetyl phosphate, alkyl sulphates (sodium cetyl sulphate), alkali metal salts of cholesterol sulphate or of cholesterol phosphate, the sodium salt of phosphatidic acid, and lipoamino acids and the salts thereof, such as the sodium acylglutamates.

The composition of the invention may additionally contain all the components conventionally used in the cosmetics field and in particular a vegetable oil, mineral oil, silicone-containing oil or synthetic oil which is dispersed in an aqueous phase, and also hydrophilic adjuvants such as gelling agents, preserving agents, opacifying agents, lipophilic adjuvants such as perfumes, pigments and fillers, as described in the documents FR-A-2,490,504 and FR-A-2,485,921. The dispersed oil may represent from 2% to 40% by weight relative to the total weight of the composition and the adjuvants may represent from 0.1 to 10% by weight.

Examples of lipid vesicles (vesicles of the first category) delivering the spin trap into the deep layers of the skin which may be mentioned are vesicles obtained from the following lipids (CTFA name):

A/cholesterol/casein lipoamino acid, especially in 45/45/10 weight ratio (where A is a triglyceryl cetyl ether marketed by the company Chimex under the name CHIMEXANE NL);

B/cholesterol/dicetyl phosphate, especially in a 60/35/5 weight ratio (where B is a mixture of triglyceryl mono-, di- and tricetyl ether, marketed by the company Chimex under the name CHIMEXANE NT);

Span 40 (from ICI, or sorbitan palmitate)/cholesterol/sodium acylglutamate (marketed under the name HS11 by the company Ajinomoto), especially in a 47.5/47.5/5 weight ratio;

PEG 8 stearate/cholesterol/sodium acylglutamate, especially with a 47.5/47.5/5 weight ratio (where PEG 8 stearate is polyethylene glycol containing 8 units of ethylene oxide, marketed by Unichema under the name PEG 400 stearate);

PEG 8 stearate/cholesterol/phytanEtriol/sodium acylglutamate, especially with a 47.5/20/27.5/5 weight ratio;

Hydrogenated lecithin/polyoxyethylenated phytosterol containing 5 units of ethylene oxide, especially in a 60/40 weight ratio;

Polyoxyethylenated methylglucose distearate containing 20 units of ethylene oxide/cholesterol/sodium acylglutamate, especially in a 45/45/10 weight ratio (the distearate being, for example, that marketed under the name GLUCAM E 20 distearate by Amerchol);

A/cholesterol/dicetyl phosphate, especially with a 47.5/47.5/5 weight ratio (where A is a triglyceryl cetyl ether marketed by the company Chimex under the name CHIMEXANE NL);

Diglyceryl distearate (for example that marketed by Nihon under the name EMALEX DS G2)/cholesterol/sodium acylglutamate, in a 45/45/10 weight ratio;

Sucrose mono- and distearate (for example GRILLOTEN PSE 141 G from Grillo)/cholesterol/sodium acylglutamate, especially in a 45/45/10 weight ratio;

Tetraglyceryl tristearate (for example TETRAGLYN 3S from Nikkol)/cholesterol/sodium acylglutamate, especially in a 45/45/10 weight ratio.

Examples of vesicles (of the second category) delivering an agent which is active at the surface into the surface layers of the skin (for example a screening agent or a moisturizing agent) which may be mentioned are vesicles obtained from the following lipids:

Sunflower lecithin;

NATIPIDE II (soya lecithin/ethanol/water in a 60/20/20 weight ratio, marketed by Nattermann);

C (soya lecithin/cholesterol/propylene glycol in a 40/30/30 weight ratio, marketed by Nattermann under the name NAT 50 PG);

D/dimyristyl phosphate, especially in a 95/5 weight ratio (where D is a lauryl polyglyceryl-6-cetearyl glycol ether marketed by Chimaxunder the name CHIMRXANE NS).

Table I below gives, for some of the lipid vesicles obtained using the above lipids, the diffusion constant D for ASL in the *stratum cornsum* and in the epidermis/dermis, as well as the degree of encapsulation of glucose and the phase transition temperature of the main lipid constituting the membrane. The diffusion constant was measured for an encapsulated ASL concentration of 0.35% by weight relative to the total weight of the composition.

TABLE I

| Ref. | LIPID SYSTEMS | Proportions % by weight (mg) | Diffusion coefficient $D$ in $10^{-7}$ cm$^2$ s$^{-1}$ | | Degree of encapsulation of glucose in µl/mg | | Phase transition temperature in °C. |
|---|---|---|---|---|---|---|---|
| | | | in the stratum corneum | in the epidermis/ dermis | $T_o$ | $T_{24h}$ | |
| | 1st type - deep down | | | | | | |
| 1 | A/cholesterol/casein lipoamino acid | 45/45/10 (67.5/67.5/15) | 42 | 5 | 7.5 | 6.8 | 50 |
| 2 | B/cholesterol/dicetyl phosphate | 60/35/5 (90/52.5/7.5) | 58 | 2 | 11.1 | 11.1 | 54 |
| 3 | Span 40/cholesterol/ sodium acylglutamate | 47.5/47.5/5 (71.25/71.25/7.5) | 42 | 2 | 13.8 | 13.8 | 50 |
| 4 | PEG 8 stearate/ cholesterol/sodium acylglutamate | 47.5/47.5/5 (71.25/71.25/7.5) | 42 | 2 | 14.4 | 14.4 | 55 |

TABLE I-continued

| | | Diffusion coefficient $D$ in $10^{-7}$ cm$^2$ s$^{-1}$ | | Degree of encapsulation of glucose in µl/mg | | Phase transition temperature |
|---|---|---|---|---|---|---|
| | Proportions % by weight | in the stratum | in the epidermis/ | | | |
| Ref. LIPID SYSTEMS | (mg) | corneum | dermis | $T_o$ | $T_{24h}$ | in °C. |
| 5 PEG 8 stearate/ cholesterol/phytanetriol/ sodium acylglutamate | 47.5/20/27.5/5 (71.25/30/ 41.25/7.5) | 8.3 | 2.5 | 4.1 | 3.0 | 55 |
| 6 Hydrogenated lecithin/ polyoxyethylenated phytosterol 2nd type - surface | 60/40 (90/60) | 8 | 2 | 6.0 | 4.8 | 80 |
| 7 Sunflower lecithin | 100 (150) | 0.3 | 0.2 | 1.6 | 0 | <0 |
| 8 Natipide II (soya lecithin/ethanol/water) | 20/16/64 (30/24/96) | 0.4 | 0.2 | 0.4 | 0 | <0 |
| 9 C (soya lecithin/ sterols/propylene glycol) | 60/20/20 (90/30/30) | 0.25 | 0.1 | 1.8 | 0 | <0 |
| 10 D/dimyristyl phosphate | 95/5 (142.5/7.5) | 0.3 | 0.2 | 2.0 | 0 | 14 |

Measurement of the degree of encapsulation is carried out as described in the RRC New document cited above, and that of the diffusion constant D is carried out as described above.

In order to recognize the state of the vesicles, the phase (fluid-gel lamellar) transition temperature of the main lipid constituting the membrane thereof is determined by differential thermal analysis (DTA).

Another subject of the invention is a process for the light-protective, anti-ageing and/or anti-acne treatment of the skin, consisting in applying to the skin the composition defined above.

Other characteristics and advantages of the invention will emerge more clearly from the description which follows, which is given as an illustration and with no limitation being applied, in reference to the single FIGURE attached which represents curves showing the inhibition of the peroxidation of sebum (a lipidic liquid produced at the skin surface) by nitroxide radicals. These tests were performed with simple compositions containing from 0.05% to 1% by weight of nitroxide radicals relative to the weight of the composition, the remainder of the composition consisting of water. These tests were performed ex vivo, placing the various compositions in contact with sebum and then irradiating them with UVA at a dose of 5 joules per cm$^2$ of sample.

The radicals tested are 2,2,6,6-tetramethylpiperidine 1-oxide (TPO), 4-hydroxytetramethylpiperidine 1-oxide (HTPO), N-tertbutyl-alpha-phenylnitrone (TBP) and doxylcyclohexane (DHNO), and correspond respectively to the curves a, b, c and d of the FIGURE.

From these curves, a weak inhibition of the peroxidation of sebum is observed in the concentration range between 0% and 0.1% with TPO, HTPO and TBP. This inhibition is close to that obtained with BHT at the same concentration. In the case of DHNO, an inhibition superior to that of BHT is observed.

This inhibition becomes greater with 1% of active agent. It is at a maximum with DHNO and HTPO, 78% and 75% inhibition respectively as against 30% with TPO and 50% with TBP.

Consequently, these four radical nitroxides have a certain effectiveness against the peroxidation of sebum.

Other features of the invention will become apparent in the course of the following descriptions of exemplary embodiments which are given for illustration of the inventions and are not intended to be limiting thereof.

The total weight of vesicle contained in the composition is preferably from 1 to 90 wt. %, more preferably from 5 to 70 wt. %, most preferably from 5 to 20 wt. % based on the total weight of the composition.

The ratio of the amount of vesicles of the first dispersion type which are capable of penetrating into the deep layers to the second dispersion type which are capable of penetrating into the surface layers is preferably from 1:9 to 9:1, more preferably from 3:7 to 7:3, most preferably from 4:6 to 6:4.

Within the context of the following examples the term qs 100 g is an amount needed to bring the total amount of the composition to 100 g.

The manufacture of compositions based on lipid vesicles acting at the surface and lipid vesicles with deep-down action, in accordance with the invention, using a nitroxide radical as active agent with deep-down action, is described below.

A) Production of Lipid Vesicles Containing ASL

The constituent lipids of the wall of the vesicles are weighed out and dissolved in 10 ml of methanol. The alcoholic solution is then transferred into a 50-ml roundflask with a ground joint, which is subsequently placed on a rotary evaporator such that the contents are thermostatted at a temperature of 30° C. The evaporation is continued until a dry film of lipid is deposited on the walls of the flask.

3 ml of an aqueous 0.01 molar solution of ASL are then added to the roundflask, which is subsequently shaken by hand for about 10 minutes, either at room temperature (20° C.) in the case of the vesicles of Table I of reference Nos. 7 to 10, or at a temperature of 50° C. in the case of the vesicles of reference Nos. 1 to 6 of Table I. The medium is then left to equilibrate at room temperature for 2 hours, after which the dispersion is placed in a dialysis bag and in contact with 500 ml of distilled water. Dialysis takes place overnight. The next day, the water is changed and the dialysis is continued for a further 4 hours.

A cotton thread 0.3 mm thick is then soaked in the vesicle dispersion and then placed in contact with a section of skin cut from a pig's ear which has been freshly taken from an abattoir intended for food supply.

The ear sample taken is rinsed with water and cut into slices 1 mm thick, 5 mm wide and 10 mm long and then placed in a maintenance cell. Measurements of the diffusion of ASL in the skin are made in the 24 hours following the taking of the skin sample.

B) Production of the Cosmetic Composition

1—Production of Vesicles of First Category (Diffusing Deep Down)

The vesicles (with deep-down action) are prepared according to a usual method for co-fusion of the various membrane constituents chosen (see Table I). Thus, the membrane constituent having the lowest melting point $T_m$ is melted. The other membrane constituents are added and the mixture is then homogenized with moderate stirring and is finally partially hydrated, while maintaining the melting temperature $T_m$ defined above.

An aqueous solution of a spin trap for the deep-down treatment is added to the paste obtained. The mixture is stirred with a turbine for 1 h, 30 min in order to hydrate fully, while maintaining the temperature $T_m$. One or more other types of active agent for the deep-down treatment are optionally added to the reaction medium (for example proteins, sugars, trace elements, essential oils), homogenization is carried out and the temperature of the medium is lowered to room temperature (20° C.).

2—Production of Vesicles of the Second Category (Diffusing at the Surface)

An aqueous solution of a screening agent or several other active agents (for example polyols, amino acids, sugars, keratolytic agents, vitamins) for the surface treatment is introduced, at room temperature (20° C.) and with simple stirring, into the chosen mixture of constituents which are to form the membrane of the vesicles acting at the surface (see Table I). Vesicles acting at the surface encapsulating the screening agent or any other active agent acting at the surface are thus obtained.

3—Production of the "Double-Liposome" Composition

The fatty phase (the oils) of the composition is added to the medium containing the vesicles with deep-down action and it is dispersed (at room temperature) with stirring. The reaction medium obtained is then mixed with that containing the vesicles acting at the surface. The adjuvants, such as preserving agents, a gelling agent which may be neutralized if necessary with a base (triethanolamine or sodium hydroxide), and fragrances, etc., are then optionally added.

The product obtained is in the form of a soft and smooth white cream which may be used in the cosmetic and/or dermatological field for protecting the skin against light radiation (visible and UV) and for combating ageing of the skin and/or acne, at the surface and deep down. This cream may be used daily.

Specific examples of cosmetic compositions in accordance with the invention are given below. The amounts are given as a percentage by weight.

EXAMPLE 1

Light-Protective Double-Liposome Cream

| Liposomes with deep-down action: | |
|---|---|
| Triglyceryl cetyl ether/cholesterol/dicetyl phosphate in a 47.5/47.5/5 weight ratio | 3.0% |
| TPO (active agent) | 1.0% |
| Demineralized water | 15.0% |
| Liposomes acting at-the surface: | |
| Soya lecithin | 3.0% |
| Benzene-1,4-di(3-methylidene-10-camphorsulphonic) acid (screening agent) | 0.5% |
| Triethanolamine (neutralizing agent) | 0.3% |
| Glycerine (active agent) | 3.0% |
| Demineralized water | 15.0% |
| Aqueous phase: | |
| Carboxyvinyl polymer (gelling agent) | 0.4% |
| Preserving agents | 0.3% |
| Triethanolamine | qs pH = 6 |
| Demineralized water | qs 100% |
| Fatty phase: | |
| Plant oils or mineral oils | 10.0% |
| Volatile silicone oil | 5.0% |

EXAMPLE 2

Depigmenting Double-Liposome Cream

This cream differs from that of Example 1 in that TBP in used as active agent with deep-down action, in place of TPO.

EXAMPLE 3

Anti-Ageing Double-Liposome Cream

| Vesicles with deep-down action: | |
|---|---|
| PEG 8 stearate/cholesterol/sodium acylglutamate in a 47.5/47.5/5 weight ratio | 5.0% |
| HTPO (membrane active agent) | 1.0% |
| Demineralized water | 15.0% |
| Fatty phase: | |
| Plant oil | 10.0% |
| Volatile silicone oil | 5.0% |
| Aqueous phase: | |
| Preserving agents | 0.3% |
| Glycerine (active agent) | 3.0% |
| Carboxyvinyl polymer (gelling agent) | 0.4% |
| Triethanolamine | qs pH = 6 |
| Water | qs 100% |

EXAMPLE 4

Anti-Acne Double-Liposome Cream

| Vesicles with deep-down action: | |
|---|---|
| Sorbitan palmitate/cholesterol/sodium acylglutamate in a 47.5/47.5/5 weight ratio | 4.0% |
| DHNO (water-soluble active agent) | 0.2% |
| Demineralized water | 15.0 |
| Vesicles acting at the surface: | |
| CHIMEXANE NS/dimyristyl phosphate in a 95/5 weight ratio | 3.0% |
| Octyl methoxycinnamate marketed under the name PARSOL MCX by the company Givaudan | 0.3% |
| Glycerol (active agent) | 3.0% |
| Demineralized water | 15.0% |
| Fatty phase: | |

-continued

| | |
|---|---|
| Plant oil | 3.0% |
| Volatile silicone oil | 4.5% |
| Aqueous phase: | |
| Triclosan | 0.2% |
| Preserving agents | 0.3% |
| Carboxyvinyl polymer (gelling agent) | 0.9% |
| Sodium hydroxide | qs pH = 6 |
| Demineralized water | qs 100% |

Obviously, numerous modifications and variations of the present invention are possible in light of the above teachings. It is therefore to be understood that within the scope of the appended claims, the invention may be practiced otherwise than as specifically described herein.

This application is based on French Patent Application 93/15869, filed with the French Patent Office on Dec. 30, 1993, the entire contents of which are hereby incorporated by reference.

What is claimed as new and desired to be secured by Letters Patent of the United States:

1. A method for treating skin comprising applying to the skin of a patient in need thereof, an effective amount of a cosmetic or dermatological composition comprising a spin trap, employed as an electron paramagnetic resonance measurement probe, to affect the light-protective, anti-ageing and/or anti-acne treatment of the skin, wherein said spin trap is present in an amount of from 0.001% to 5% by weight relative to the total weight of the composition.

2. The method of claim 1, wherein said spin trap is selected from the group consisting of a stable cyclic nitroxide comprising at least one ring containing a nitrogen atom which is bonded to the oxygen atom and a stable nitrone radical comprising at least one ring containing a nitrogen atom which is bonded to the oxygen atom.

3. The method of claim 2, wherein said spin trap comprises alkyl groups in n position $\alpha$ to said nitrogen atom.

4. The method of claim 2, wherein said spin trap is selected from the group consisting of 2,2,6,6-tetramethylpiperidine 1-oxide radical, 4-hydroxytetramethylpiperidine 1-oxide radical, N-tertbutyl-$\alpha$-phenylnitrone radical, doxylcyclohexane radical, and N-(1-oxyl-2,2,6,6-tetramethyl-4-piperidyl)-N,N-dimethyl-N-hydroxyethylammonium salts.

5. The method of claim 2, wherein, said spin trap is in an amount of from 0.1% to 2% by weight relative to the total weight of the composition.

6. The method of claim 2, wherein said spin trap is encapsulated in spherules.

7. The method of claim 6, wherein said spherules are lipid vesicles.

8. The method of claim 6, wherein said spherules comprise spherules with deep-down action which are capable of diffusing into the deep layers of the skin.

9. The method of claim 8, wherein said spherules with deep-down action are in a gelled state at room temperature.

10. The method of claim 8, wherein said spherules with deep-down action are formed of lipids comprising at least one linear and saturated fatty chain having from 16 to 30 carbon atoms.

11. The method of claim 8, wherein said spherules with deep-down action are formed of lipids selected from the group consisting of triglyceryl cetyl ether/cholesterol/casein lipoamino acid;

a mixture of triglyceryl moro-, di- and tricetyl ether/cholesterol/dicetyl phosphate;

triglyceryl cetyl ether/cholesterol/dicetyl phosphate;

sorbitan palmitate/cholesterol/sodium acylglutamate;

PEG 8 stearate/cholesterol/sodium acylglutamate;

diglyceryl distearate/cholesterol/sodium acylglutamate;

sucrose mono- and distearate/cholesterol/sodium acylglutamate;

PEG 8 stearate/cholesterol/phytanetriol/sodium acylglutamate;

polyoxyethylenated methylglucose distearate containing 20 mol of ethylene oxide/cholesterol/sodium acylglutamate;

hydrogenated lecithin/polyoxyethylenated phytosterol; and tetraglyceryl tristearate/cholesterol/sodium acylglutamate.

12. The method of claim 1, wherein said cosmetic or dermatological composition is provided in the form of a gel, an emulsion, a lotion, a serum or oil droplets dispersed by lipid vesicles.

13. The method of claim 1, wherein said cosmetic or dermatological composition further comprises an oily phase which is dispersed in an aqueous phase.

14. The method of claim 1, wherein said cosmetic or dermatological composition further comprises hydrophilic adjuvants.

15. The method of claim 1, wherein said cosmetic or dermatological composition further comprises a sunscreen, agent.

16. The method of claim 15, wherein said sunscreen agent is encapsulated in spherules active at the surface which are capable of diffusing into the surface layers of the skin.

17. The method of claim 16, wherein said vesicles active at the surface are formed of lipids selected from the consisting of natural ionic phospholipids containing unsaturated fatty chains having from 16 to 30 carbon atoms, polyol alkyl ethers or polyol alkyl esters having at least one fatty chain per molecule, including at least one fatty chain with a length of less than 16 carbon atoms, and mixtures thereof.

18. The method of claim 16, wherein said spherules active at the surface are formed of at least one lipid selected from the group Consisting of: Sunflower lecithin, Soya lecithin/ethanol/water, Soya lecithin/cholesterol/propylene glycol and Lauryl polyglyceryl-6-cetearyl glycol ether/dimyristyl phosphate.

* * * * *